United States Patent
Echavarry

(10) Patent No.: US 10,034,907 B1
(45) Date of Patent: Jul. 31, 2018

(54) FLAVORED AND EDIBLE CANNABINOID COMPOSITION AND METHOD OF MANUFACTURING

(71) Applicant: Gerald Echavarry, New Hyde Park, NY (US)

(72) Inventor: Gerald Echavarry, New Hyde Park, NY (US)

( * ) Notice: Subject to any disclaimer, the term of this patent is extended or adjusted under 35 U.S.C. 154(b) by 14 days.

(21) Appl. No.: 15/481,657

(22) Filed: Apr. 7, 2017

(51) Int. Cl.
| | |
|---|---|
| *A61K 36/00* | (2006.01) |
| *A61K 36/185* | (2006.01) |
| *A61K 47/10* | (2017.01) |
| *A61K 9/00* | (2006.01) |

(52) U.S. Cl.
CPC .......... *A61K 36/185* (2013.01); *A61K 9/0056* (2013.01); *A61K 47/10* (2013.01)

(58) Field of Classification Search
CPC ..................................................... A61K 36/00
USPC ......................................... 424/725
See application file for complete search history.

(56) References Cited

U.S. PATENT DOCUMENTS

| | | |
|---|---|---|
| 6,403,126 B1 | 6/2002 | Webster et al. |
| 8,906,429 B1 | 12/2014 | Kolsky |
| 2011/0256245 A1 | 10/2011 | Rosenblatt et al. |
| 2015/0057341 A1 | 2/2015 | Perry |
| 2015/0126754 A1 | 5/2015 | Cid et al. |
| 2018/0042845 A1* | 2/2018 | Sinai .................... A61K 9/1075 |

\* cited by examiner

*Primary Examiner* — Michael V Meller
(74) *Attorney, Agent, or Firm* — Global Intellectual Property Agency, LLC; Daniel Enea

(57) ABSTRACT

A flavored cannabinoid composition and method of manufacturing. The cannabinoid composition includes a cannabis resin, a solvent, such as propylene glycol, and a flavoring agent selected from the following group consisting of Cinnamaldehyde, Isoamyl acetate, d-limonene, Methyl anthranilate, vanilla extract, chocolate extract, and Allyl hexanoate. The cannabinoid composition is administered via inhalation or consumption of food and drink to complement or supplement other medications.

4 Claims, No Drawings

FLAVORED AND EDIBLE CANNABINOID COMPOSITION AND METHOD OF MANUFACTURING

CROSS REFERENCE TO RELATED APPLICATION

This application claims the benefit of U.S. Provisional Application No. 62/231,772 filed on Nov. 6, 2015. The above identified patent application is herein incorporated by reference in its entirety to provide continuity of disclosure.

BACKGROUND OF THE INVENTION

Field of the Invention

The present invention relates to an edible cannabinoid composition. More specifically, the present invention provides a flavored edible cannabinoid composition and method of making thereof.

Cannabis, and other cannabinoids, have been used to alleviate stress and other illnesses caused by posttraumatic stress disorder, seizures, epilepsy, multiple sclerosis, and the like. Cannabis, more commonly known as marijuana, is a genus of flowering plants that includes at least three species, Cannabis sativa, Cannabis indica, and Cannabis ruderalis. The use of cannabis for social and medical purposes has been known for almost of all humanity's recorded history. Cannabis is most commonly administered via inhalation or consumption of marijuana-infused food and drink. Further, cannabinoid compositions are often used to complement or supplement other medications.

Since 1972 marijuana has been classified as a Schedule I drug under the U.S. Controlled Substances Act because the U.S. Federal Government considers it to have "no accepted medical use." In stark contrast to this position, 25 of the 50 U.S. states and the District of Columbia have recognized the medical benefits of cannabis and have decriminalized its medical use. Despite the official position of the U.S. Federal Government and as recognized by the states that have legalized it, cannabis has been shown to provide substantial and varied medical benefits. Cannabis is regularly used by a wide cross-section of society to treat a variety of maladies, conditions and symptoms including, but not limited to, the following: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

Compositions and methods of manufacturing have been disclosed in the known art that relate to compositions that include cannabinoids. These include compositions that have been patented and published in patent application publications.

SUMMARY OF THE INVENTION

In view of the foregoing disadvantages inherent in the known types of cannabinoid compositions now present in the art, the present invention provides a new cannabinoid composition wherein the same can be utilized for administered via inhalation or consumption of marijuana-infused food and drink.

It is therefore an object of the present invention to provide a new and improved cannabinoid composition. The cannabinoid composition comprises cannabis resin, a solvent, such as propylene glycol, and a flavoring agent selected from the following group consisting of Cinnamaldehyde, Isoamyl acetate, d-limonene, Methyl anthranilate, vanilla extract, chocolate extract, and Allyl hexanoate It is another object of the present invention to provide a method manufacturing a cannabinoid composition for administered via inhalation or consumption of marijuana-infused food and drink. The method of manufacturing the cannabinoid composition includes heating cannabis resin to a temperature between 110 degrees and 140 degrees Fahrenheit; mixing the cannabis resin with a solvent to form a cannabis solution; mixing a flavoring agent with the cannabis solution; wherein the flavoring agent is selected from the following group consisting of Cinnamaldehyde, isoamyl acetate, d-limonene, Methyl anthranilate, vanilla extract, chocolate extract, and Allyl hexanoate.

Another object of the present invention is to provide a cannabinoid composition that may be readily fabricated from materials that permit relative economy and are commensurate with consumption.

Other objects, features and advantages of the present invention will become apparent from the following detailed description.

DETAILED DESCRIPTION OF THE INVENTION

The present invention provides a cannabinoid composition that is flavored and can be utilized for administered via inhalation or consumption. The cannabinoid composition comprises cannabis resin, a solvent, such as propylene glycol, and a flavoring agent selected from the following group consisting of Cinnamaldehyde, Isoamyl acetate, d-limonene, Methyl anthranilate, vanilla extract, chocolate extract, and Allyl hexanoate. Each of the flavoring agents have a distinct flavor, wherein Cinnamaldehyde has a cinnamon flavor, Isoamyl acetate has a banana flavor, d-limonene citrus has a flavor, Methyl anthranilate has a grape flavor, vanilla extract has a vanilla flavor, chocolate extract has a chocolate flavor, and Allyl hexanoate has a pineapple flavor. The solvent is an ingestible solvent.

In one embodiment, the cannabinoid composition includes two grams cannabis resin, between one to three milliliters of the solvent propylene glycol, and between one to three milliliters of the flavoring agent. The cannabinoid composition may be administered via inhalation or consumption. The cannabis resin may be manufactured from ground cannabis that is frozen, mixed with a solvent, filtered, and distilled. The resulting cannabis resin is also called cannabis oil, shatter, or wax.

The method of manufacturing the cannabinoid composition includes heating cannabis resin to a temperature between 110 degrees and 140 degrees Fahrenheit; mixing the cannabis resin with a solvent to form a cannabis solution; mixing a flavoring agent with the cannabis solution wherein the flavoring agent is selected from the following group consisting of Cinnamaldehyde, Isoamyl acetate, d-limonene, Methyl anthranilate, vanilla extract, chocolate extract, and Allyl hexanoate.

In one embodiment, the cannabis resin of the cannabinoid composition is heated between 110 degrees and 140 degrees Fahrenheit within a water bath. The cannabis resin is heated for approximately two minutes, or when the cannabis resin is in a liquid state. The water bath helps to control and regulate the temperature as the cannabis resin is being heated. The cannabis resin is preferably in a liquid state for better mixing with the solvent.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of manufacturing a cannabinoid composition, consisting essentially of:
   heating a *cannabis* resin to a temperature between 110° F. and 140° F.;
   mixing the *cannabis* resin with propylene glycol to form a *cannabis* solution;
   mixing a flavoring agent with the *cannabis* solution;
   wherein the flavoring agent is selected from the following group consisting of Cinnamaldehyde, Isoamyl acetate, d-limonene, Methyl anthranilate, vanilla extract, chocolate extract, and Allyl hexanoate to yield said cannabinoid composition.

2. The method of manufacturing a cannabinoid composition of claim 1, wherein the *cannabis* resin consists essentially of two grams.

3. The method of manufacturing a cannabinoid composition of claim 1, wherein the propylene glycol consists essentially of between one to three milliliters.

4. The method of manufacturing a cannabinoid composition of claim 1, wherein the flavoring agent consists essentially of between one to three milliliters.

* * * * *